United States Patent
Lualdi (10) Patent No.: US 7,645,273 B2
(45) Date of Patent: Jan. 12, 2010

(54) VASCULAR CATHETER GUIDE WIRE CARRIER

(75) Inventor: Alessandro Lualdi, Luxembourg (LU)

(73) Assignee: EVR Medical S.A.R.L., Luxembourg (LU)

( * ) Notice: Subject to any disclaimer, the term of this patent is extended or adjusted under 35 U.S.C. 154(b) by 1217 days.

(21) Appl. No.: 10/469,673

(22) PCT Filed: Mar. 12, 2002

(86) PCT No.: PCT/IB02/00722

§ 371 (c)(1),
(2), (4) Date: Jun. 1, 2004

(87) PCT Pub. No.: WO02/072186

PCT Pub. Date: Sep. 19, 2002

(65) Prior Publication Data

US 2004/0220473 A1    Nov. 4, 2004

Related U.S. Application Data

(60) Provisional application No. 60/275,832, filed on Mar. 14, 2001.

(51) Int. Cl.
*A61M 25/00*    (2006.01)
(52) U.S. Cl. .................................................... 604/523
(58) Field of Classification Search ............. 604/96.01, 604/523, 264, 103.1, 524–539, 284
See application file for complete search history.

(56) References Cited

U.S. PATENT DOCUMENTS 4,552,554 A    11/1985 Gould et al.
4,769,005 A    9/1988 Ginsburg et al.
4,894,057 A *  1/1990 Howes ........................ 604/523

(Continued)

FOREIGN PATENT DOCUMENTS

EP    792627 A2    9/1997

(Continued)

OTHER PUBLICATIONS

European Search Report, Application No. 02 714 365.0—2310, Ref. E054089-PC.

(Continued)

*Primary Examiner*—Manuel A Mendez
(74) *Attorney, Agent, or Firm*—Polster, Lieder, Woodruff & Lucchesi, LC (57) ABSTRACT

A carrier catheter (20) for the introduction and positioning or changing of one or more guidewires (GW1, GW2, GW3) or interventional devices in a vessel V in the body of a subject. The catheter (20) includes an elongated, thin flexible body (22) having a primary lumen (24) and ancillary lumens (26, 28). Each lumen has an opening at the proximal end and an opening (30, 32, 34) at the distal end to permit a guidewire or device to extend through and exit the lumen. The openings at the distal ends of the lumens are positioned so that the respective guidewires or interventional devices can exit the lumens at different locations along the distal end of the catheter. One introduction of the device allows the deployment of any combination of multiple guidewires and interventional devices. The catheter can be used for a rapid replacement of an indwelling catheter or rapid replacement of a dedicated guidewire.

20 Claims, 6 Drawing Sheets

U.S. PATENT DOCUMENTS

| | | | |
|---|---|---|---|
| 4,932,413 A | | 6/1990 | Shockey et al. |
| 4,947,864 A | | 8/1990 | Shockey et al. |
| 5,059,177 A | * | 10/1991 | Towne et al. ........... 604/102.02 |
| 5,395,316 A | * | 3/1995 | Martin ........................ 604/43 |
| 5,413,557 A | | 5/1995 | Solar |
| 5,795,331 A | | 8/1998 | Cragg et al. |
| 5,908,446 A | | 6/1999 | Imran |
| 6,096,073 A | | 8/2000 | Webster et al. |
| 6,143,002 A | | 11/2000 | Vietmeier |
| 6,190,352 B1 | | 2/2001 | Haarala et al. |
| 6,682,536 B2 | * | 1/2004 | Vardi et al. ................. 606/108 |
| 2002/0055733 A1 | | 5/2002 | Wilson |

FOREIGN PATENT DOCUMENTS

| | | |
|---|---|---|
| EP | 897700 A1 | 2/1999 |
| EP | 1368086 B1 | 12/2007 |
| JP | 11226131 A2 | 8/1999 |
| WO | 9915103 | 4/1999 |
| WO | 0145785 A2 | 6/2001 |
| WO | 02072186 A3 | 9/2002 |

OTHER PUBLICATIONS

File Wrapper for EP Patent Application No. 02714365.0 filed Mar. 12, 2003 entitled "Vascular Catheter Guide Wire Carrier".

EndoSonics, Inc. package label for FloWire Doppler Guide Wire, one page, dated 2000.

PercuSurge Inc. "Instructions for Use" of the GuardWire Plus Temporary Occlussion & Aspiration System, 8 pages, undated.

* cited by examiner

VASCULAR CATHETER GUIDE WIRE CARRIER

CROSS REFERENCE TO RELATED APPLICATIONS

This application claims the benefit of U.S. Provisional Application No. 60/275,832, filed 14 Mar. 2001.

TECHNICAL FIELD

The invention relates generally to intravenous catheters and, more specifically, an intravascular carrier catheter and method for introducing intravascular catheter guidewires to support subsequent introduction or replacement of other intravenous or intra-arterial catheters or interventional devices within the coronary and peripheral vasculature, particularly in the areas of bifurcated vessels or occluded vessels.

In cardiology or cardiovascular surgery, there are a number of conditions in which it is desired to insert a catheter or other interventional device in a coronary artery or peripheral vasculature or extra-cardiological situations. For example, it may be necessary to insert a catheter in an occluded or narrowed artery so as to open the occlusion with a balloon, place a stent, position a pressure monitoring lead, or any other number of indications.

Generally speaking, in any number of the above-mentioned clinical situations, a guidewire is used to support advancement of the device in the vessel and positioned in the desired location under fluoroscopy. A catheter is introduced over the guidewire and appropriately positioned. In the clinical situation in which the patient has an occluded artery, for example, a relatively stiff guidewire is required to cross the occlusion and provide sufficient rigidity and support to the catheter. A balloon catheter may be introduced over the guidewire and the balloon inflated to open the lesion and/or to place a stent at the site of the lesion.

In the event there are lesions or stenosis at a bifurcation in the vessel, the procedure is repeated with separate catheters and guidewires inserted into branches of the bifurcation, necessitating the introduction of multiple catheters and guidewires. Also, if the physician wants to introduce other interventional devices to the vessel, such as pressure sensing leads or the like, or desires to introduce drugs to the site, more than one guidewire must be inserted and left in place so that another catheter or device can be employed. It has been known that when multiple guidewires are employed, for whatever the reason, the guidewires can become crossed or entangled within a vessel. Also, situations arise where the interventional device, for example a pressure sensing lead, is thin and does not have the rigidity to allow the operator to pass the device through a narrowed vessel or occlusion.

It also may become necessary, over time, for the physician to change an indwelling guidewire. In prior art systems, a catheter is inserted over the existing guidewire and advanced down the guidewire and crossing the lesion. Leaving the catheter in position, the guidewire is removed. A new guidewire is advanced through the catheter. The catheter then is removed. This procedure is somewhat time consuming and not without the attendant risks to the patient associated with catheterization.

It would be advantageous, therefore, to have a system that provides for the quick, safe and efficient deployment of multiple guidewires at one time so that multiple catheter-borne interventional devices may be introduced, interchangeably, over any one of the indwelling guidewires. It also would be advantageous to have a device that allows for the rapid changing of an indwelling guidewire, for example, by allowing the deployment of the replacement guidewire at the same time through the same catheter used for withdrawing the old catheter. A desired system also would allow deployment non-catheter borne devices such as fiber optic wires, pressure or flow measurement leads and the like. It also would be advantageous to have a system that allows the placement of multiple parallel guidewires while avoiding entanglement or entwining of the guidewires.

SUMMARY OF THE INVENTION

It is among the several aspects and objects of the present invention to provide an apparatus and method for the deployment of multiple guidewires or interventional devices in a vessel or vessels.

The present invention is employed as an apparatus and method for introducing, removing or changing one or more intravascular guidewires without crossing or entanglement of the guidewires.

Another aspect of the invention is to provide an apparatus and method for the introduction and positioning multiple guidewires to allow for the subsequent introduction and proper placement of interventional devices over the guidewires. A further aspect of the invention is an apparatus and method for carrying deploying in the vasculature interventional devices that ordinarily cannot be introduced across, or are difficult to introduce across, vascular occlusions. Another aspect of the invention provides an apparatus and method that is particularly adaptable for use in the presence of lesions in bifurcated vascular areas.

One aspect of the invention is an intravascular carrier catheter provided for the introduction and positioning of multiple guidewires or other devices, in a single step, generally beyond an occlusive lesion or at a bifurcation. The carrier catheter of the present invention includes an elongated, thin flexible catheter body. The catheter body includes a primary or lead lumen and, in the preferred embodiment, two additional or ancillary lumens. The invention can include a primary lumen and more or less than two ancillary lumens. In any case, the primary lumen has an opening at the proximal end and an opening at the distal end so that a lead guidewire can extend through the length of the lumen. The ancillary lumens are designed to accommodate additional guidewires or to seat interventional devices, such as sensing leads, for deployment within the vasculature. The openings at the distal ends of the lumens can be positioned offset relative to each other so as to have the respective guidewires or devices exit the lumens at different points along the distal length of the catheter.

Another embodiment of the catheter includes an introductory apparatus that can be a semi-rigid push wire, or a semi-rigid extension of the catheter body, at the proximal end and a shorter catheter body at the distal end of the push wire. In another embodiment, the catheter body is of conventional length and may include hardware, such as Luer-lok® type connection, at the proximal ends of each lumen. Either way, the opening of the primary guidewire lumen generally is positioned at the extreme distal end of the catheter with the distal openings of the second and third ancillary lumens arranged up the length of the catheter from that opening. Generally, guidewires are positioned within the second and third lumens. Other interventional devices can be employed in the ancillary lumens.

The primary lumen is placed over the proximal end of previously positioned dedicated guidewire and the catheter is introduced into the vessel or any other biological conduit over the dedicated guidewire and thus, appropriately positioned.

The second and third guidewires or devices are positioned within their respective ancillary lumens so as to not protrude from the distal openings of those lumens. The catheter includes radio-opaque markers or markings to guide placement under fluoroscopy. Once the catheter is in the desired position within the vessel, the second and third guidewires, or devices, can be advanced out of the distal openings of their ancillary lumens and into their desired positions, for example, for positioning in a bifurcation. Once the catheter is appropriately positioned and the three guidewires or devices are in the desired locations, the carrier catheter can be withdrawn and the guidewires or devices left in place. If guidewires are initially employed in the ancillary lumens and then left in place, other interventional devices can be introduced over any one of the appropriately placed guidewires.

The device of the present invention can be employed to facilitate the changing of an indwelling catheter. The indwelling catheter is withdrawn over the appropriate guide wire. The guidewire remains in place and the replacement catheter is advanced along the guidewire. With the catheter of the present invention, one catheter can be used to position three guidewires and those three guidewires can be used to introduce three separate catheters or interventional devices into the vessel In another aspect of the invention the device of the present invention can be employed to facilitate the changing of a dedicated guidewire. The primary lumen of the catheter of the present invention is introduced over the subject guidewire and positioned. The replacement guidewire is introduced through one of the ancillary lumens, which is adjacent to the lumen containing the subject guidewire. The subject guidewire is withdrawn and the catheter can be withdrawn over the new guidewire, leaving in place the new guidewire, which was introduced through the ancillary lumen and positioned where the extracted guidewire had resided. It will be appreciated that since the device of the present invention includes multiple lumens, more than one guidewire can be replaced with one catheter introduction.

Various other aspects and objects of the present invention will be apparent to those skilled in the art upon review of the following specification and the accompanying drawings.

BEST MODE FOR CARRYING OUT THE INVENTION

The invention is a versatile, multi-lumen carrier catheter that can be used for the introduction and placement of multiple guidewires or for the introduction and placement of interventional devices, including devices that can be introduced over a guidewire and devices that cannot be introduced over a guidewire. The carrier catheter also is used to replace an indwelling catheter or to change dedicated guidewires. One preferred embodiment of the novel carrier catheter of the present invention is indicated by reference numeral 20 in FIG. 1. Catheter 20 includes an elongated, generally flexible body section 22 formed from biologically compatible materials known to the art. Generally, flexible implies that the catheter is not so rigid as to increase the risk of puncture or dissection of a vessel when inserted but appropriately inflexible so as to allow it to be inserted into a vessel with a guidewire.

Figures 1, 2, 5:
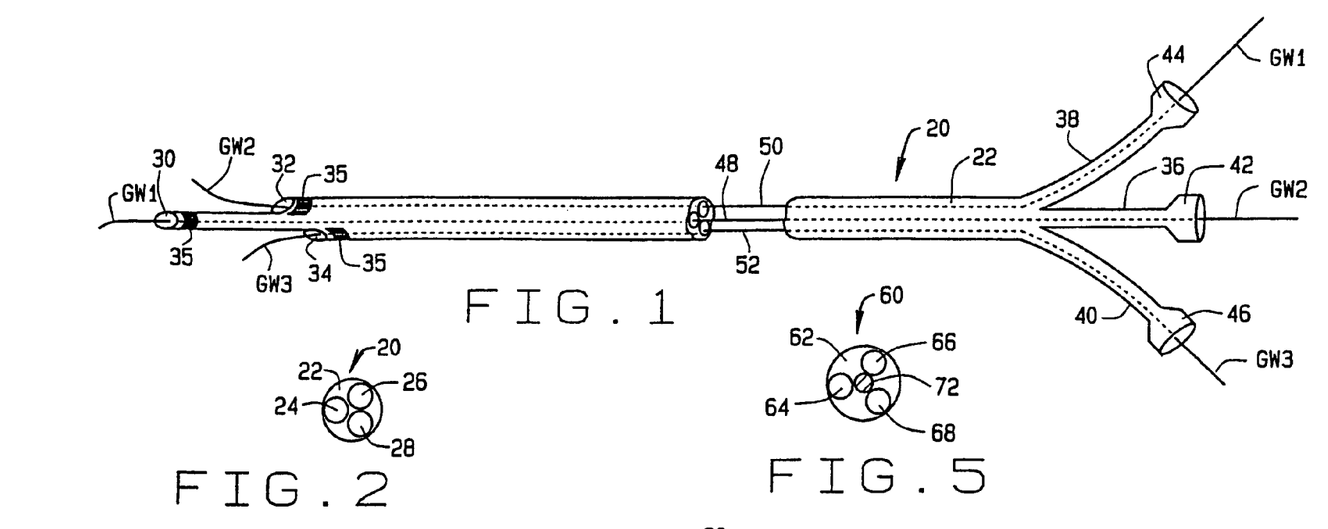
FIG. 1 is a side elevation of one preferred embodiment of the multiple wire carrier catheter of the present invention with guidewires therein.
FIG. 2 is a cross section thereof.
FIG. 5 is a cross section thereof.

As seen in FIG. 2, the body section of catheter 20 includes three inner bores or lumens 24, 26 and 28. The three lumens are contained within the body section 22 so that the cross-section of the body section is circular. Body 22 can be solid with the lumens formed therein or the lumens can be discrete elongated tubes or passageways contained within a covering to form the body. Any other construction that provides for a catheter body having three separate lumens or bores is acceptable. When the body is described or claimed as having one or more lumens, any configuration or construction of lumens is intended.

As seen in FIG. 1, the first or primary lumen 24 terminates distally in port or opening 30. This lumen also can be referred to as the lead or drive lumen in that, generally, the lead or introductory guidewire is employed in this lumen The second lumen 26 terminates distally in a port or opening 32 and the third lumen 28 terminates distally in port or opening 34. The second and third lumens can be referred to as ancillary lumens. They also can be referred to as cargo or loading lumens to reflect the fact that they can be used to carrier and deploy interventional devices other than guidewires, as will be described below.

It will be noted that in the embodiment illustrated, the distal opening 30 of the primary lumen is the distal most opening, while openings 32 and 34 are positioned up from opening 30. That is, the second and third openings 32, 34, respectively, are positioned in a proximal relationship to opening 30. It will be appreciated that openings 32, 34 can be placed at any desired location along the length of body 22, as required by the application of the catheter. For example, in the illustrated embodiment, opening 34 also is proximal to opening 32.

The body 22 can be preformed with openings 32 and 34 in the lumens located at desired locations or, if necessary, the body and lumens can be cut on the spot to create openings 32 and 34 at desired relative locations based upon a clinical evaluation of the intended use. Also, the lumens preferably include radio-opaque marks 35 adjacent the openings to allow appropriate positioning of openings 30, 32 and 34 under fluoroscopy. Any placement of radio-opaque markers or other appropriate markers along the length of the catheter that facilitate proper placement of the catheter is contemplated by the invention. The relative positions of openings 30, 32 and 34 can be arranged to optimize the use of catheter 20 in bifurcated arteries.

The proximal ends of lumens 24, 26 and 28 terminate in extensions 36, 38 and 40, respectively. In the embodiment illustrated, the extensions are integral and the terminal ends of the extensions are equipped with Luer-lok®-type connectors 42, 44 and 46, respectively. These connectors, or any other appropriate connectors or fittings known to the art, are used to attach the catheter to devices, such as syringes or the like, to facilitate introduction or placement of the catheter in a vessel or for the introduction of a pharmaceutical, such as a thrombolytic agent or any other pharmaceutical agent, through the catheter lumens. As shown, a first or lead guidewire GW1 extends through lumen 24, a second guidewire GW2 extends through lumen 26 and a third guidewire GW3 extends through lumen 28. In most applications, the standard guidewires are approximately 0.014 inch in diameter. GW1, as the lead guidewire, can have a diameter greater than the standard or more stiffness so that can endure greater torque to facilitate passage of the catheter through the vasculature and across an occlusive lesion.

Figures 3, 4:
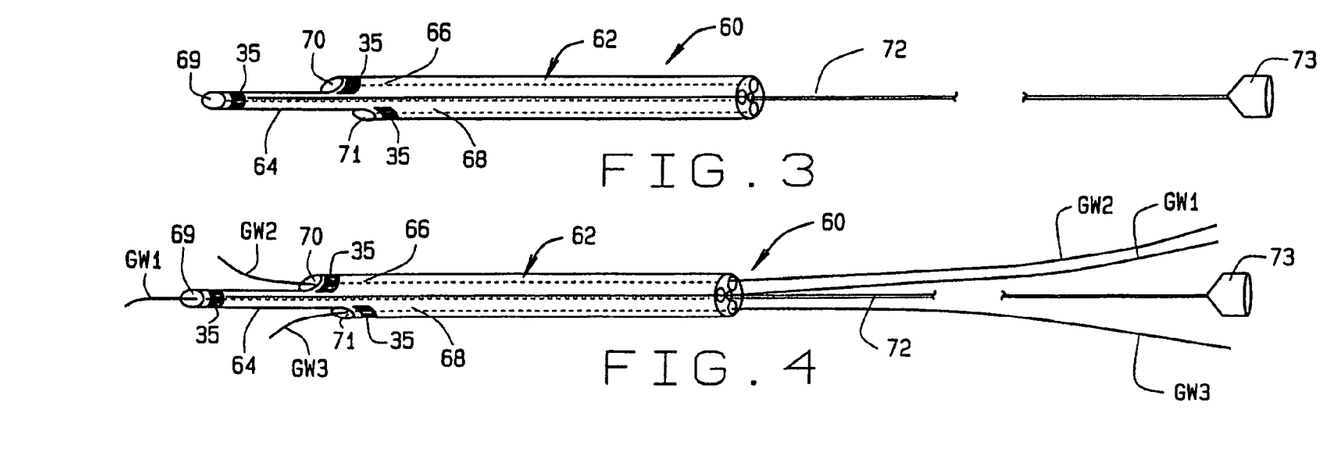
FIG. 3 is a side elevation of another embodiment of the multiple wire carrier catheter of the present invention.
FIG. 4 is a side elevation of the catheter of FIG. 3 with guidewires.

FIGS. 3, 4 and 5 illustrate another embodiment of the catheter of the present invention, indicated generally by numeral 60. Catheter 60 includes an elongated catheter body 62, which is relatively shorter than catheter body 22. However, catheter body 62 is constructed similarly to the catheter body 22. The body 62 includes inner lumens 64, 66 and 68 (FIG. 5) which terminate distally in ports or openings 69, 70 and 71, respectively. However, catheter 60 includes an introductory apparatus which can be a substantially inflexible proximal extension of the catheter body or, as shown in the illustrated embodiment, an integral push wire 72 which can include a connector or other fitting 73 at its proximal end. Push wire 72, which is formed from steel or other appropriate material, is sufficiently rigid to allow the introduction of the catheter body into position within a vein or artery when advancing down a lead guidewire positioned in lumen 64. Push wire 72 is not so inflexible so as to cause an undue risk of dissection during use. The catheter also includes external radio opaque marks 35 adjacent the openings 69, 70 and 71, as previously explained. As seen in FIG. 4, guidewires GW1, GW2 and GW3 extend through the lumens 64, 66 and 68 respectively.

Figure 6:
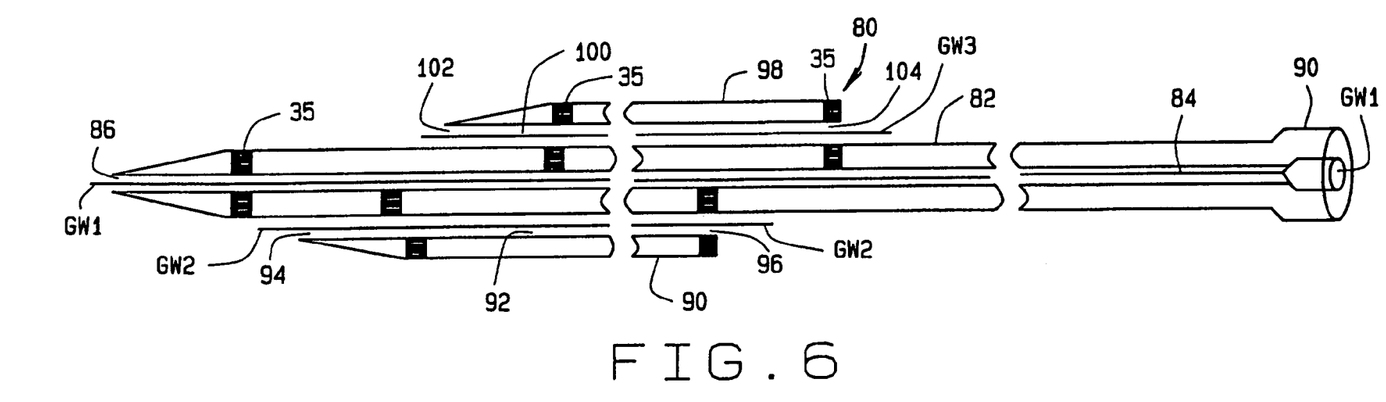
FIG. 6 is an enlarged schematic cross-section of another embodiment of the multiple wire carrier catheter of the present invention.

FIG. 6 illustrates in cross-section of yet another exemplary embodiment of the catheter of the present invention, indicated generally by numeral 80. Catheter 80 includes a main body section 82, having a primary central bore or lumen 84. There is an opening 86 of lumen 84 at the distal end of body section 82. The proximal end of body section 82 terminates in a Luer-lok®-type connection 88. The overall length of catheter 80, from the distal opening 86 to connection 88 is approximately 115 cm to approximately 135 cm.

A first ancillary body section 90 having a lumen 92 with a distal opening 94 and proximal opening 96, is positioned on one side of main body section 82. There is a second ancillary body section 98 having a lumen 100, a distal opening 102 and proximal opening 104 on another side of main body section 82. It will be noted that the distal openings 86, 94 and 102 are juxtaposed in any desired relationship so the openings to the lumens are located along the distal length of catheter 80 in desired locations. Correspondingly, proximal openings 96 and 104 are positioned as desired.

In the illustrated embodiment, second ancillary body section 98 is positioned proximally relative to the first ancillary body section. In this embodiment it is approximately 25 cm to approximately 35 cm from distal opening 86 to proximal opening 104. There are radio-opaque marks 35 adjacent the various distal and proximal openings to allow for appropriate positioning under fluoroscopy. It will be appreciated that the longitudinally contiguous portions of three body sections can have a common covering, if desired. As shown, main body section is substantially longer than the two ancillary sections. For example, a representative catheter 80 may have an overall length of 115 to 135 cm, while the length of the ancillary sections would be approximately 25 to 35 cm. In any event, each of the recited bores accommodates a guidewires GW1, GW2 and GW3. The design can be altered to include ancillary lumens of different lengths. Also, the ancillary body sections can be elastic so that lumens 96 and 104 can expand to accommodate wires or devices having a greater diameter that a standard guidewire, which, generally is about 0.014 inch. Also, lumens 96 and 104 can be tapered from a greater diameter at the proximal end to a smaller diameter at the distal end in order to facilitate introduction of interventional devices into the lumens.

With regard to catheters 20, 60 and 80 just described, the exemplary embodiments disclose carrier catheters having three lumens. It is to be understood that the construction of the respective catheters can be modified to include fewer than three and, if the diameter of the target biological conduit is sufficiently large, the bodies of the respective carrier catheters can include more than three lumens, without departing from the scope of the present invention.

Figure 7:
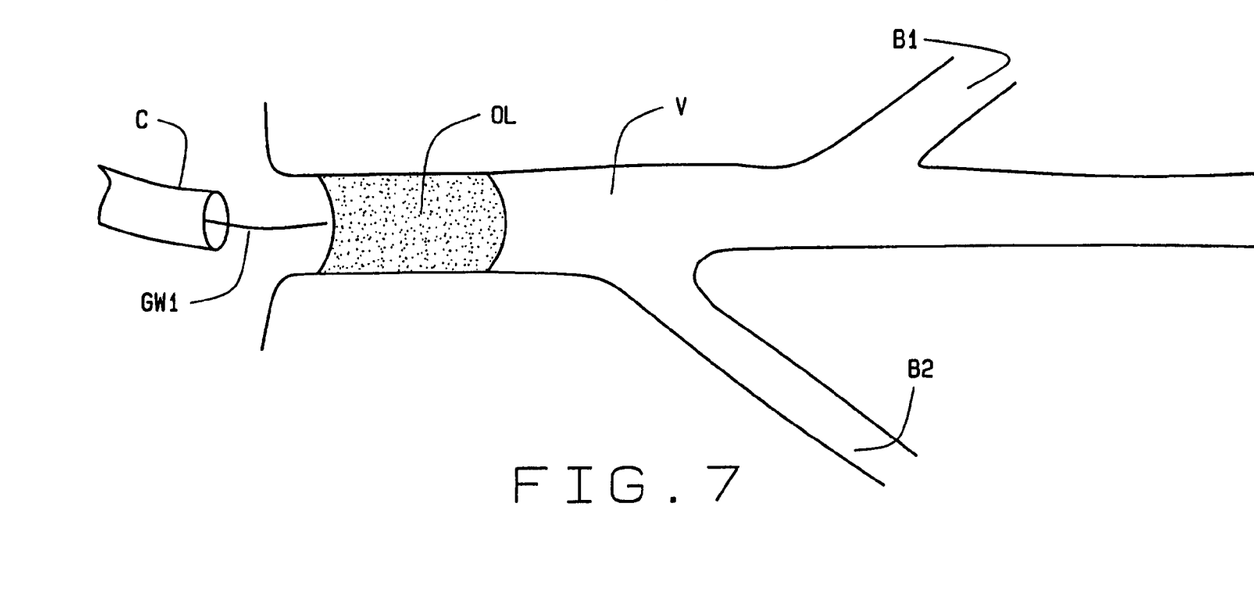
FIG. 7 illustrates an occluded vessel and the positioning of a guide catheter.
Figure 8:
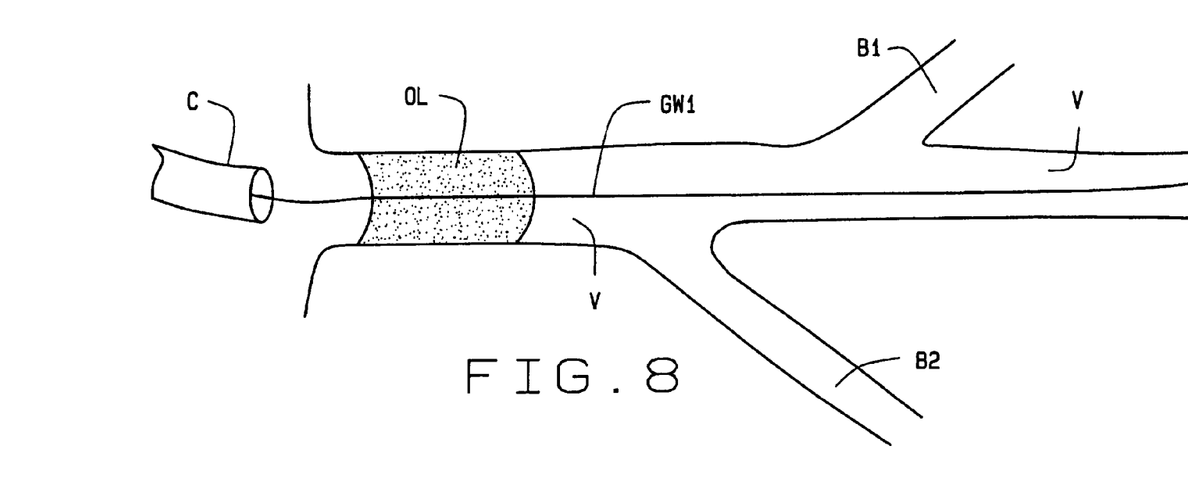
FIG. 8 illustrates the positioning of a dedicated guidewire across the occlusion.

The three illustrated exemplary embodiments of the catheter of the present invention, or modifications thereof having more or less than three lumens, can be used in similar clinical situations and each may offer some distinct advantage. The method of using the novel catheters is illustrated in FIGS. 7-14. The catheters are intended to be used in biological conduits or lumens, such as arteries, veins, tubes, ducts, canals, other vessels and similar anatomical structures, in the body of a subject in need of such use. For purposes of brevity and clarity, the term vessel is used herein to encompass all such anatomical structures. The term subject is intended to include any subject, regardless of species. One exemplary vessel is a coronary artery. One exemplary subject is a human subject. As seen in FIG. 7, an occlusive lesion OL in vessel V is documented by acceptable clinical and diagnostic methods. A conventional guide catheter C of known construction is appropriately positioned at the vessel V. A first guidewire GW1 is advanced through the guide catheter C to the site. As seen in FIG. 8, the first guidewire GW1 is advanced, crossing lesion OL and positioned in the parent vessel V with the distal tip of the wire positioned distally to or beyond the lesion. The guide catheter C is left in place during the procedure to accommodate the injection of dye into the vessel during the procedure. If desired, after injecting the dye, the guide catheter can be withdrawn.

Figure 9:
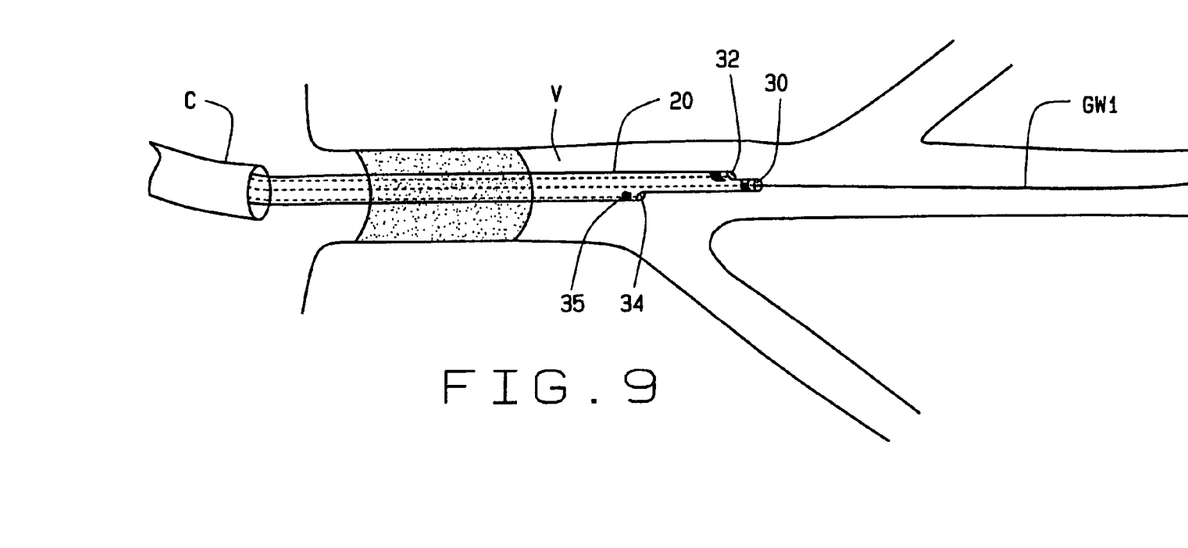
FIG. 9 illustrates the positioning of the dedicated guidewire in a catheter of the present invention over the dedicated guidewire.
Figure 10:
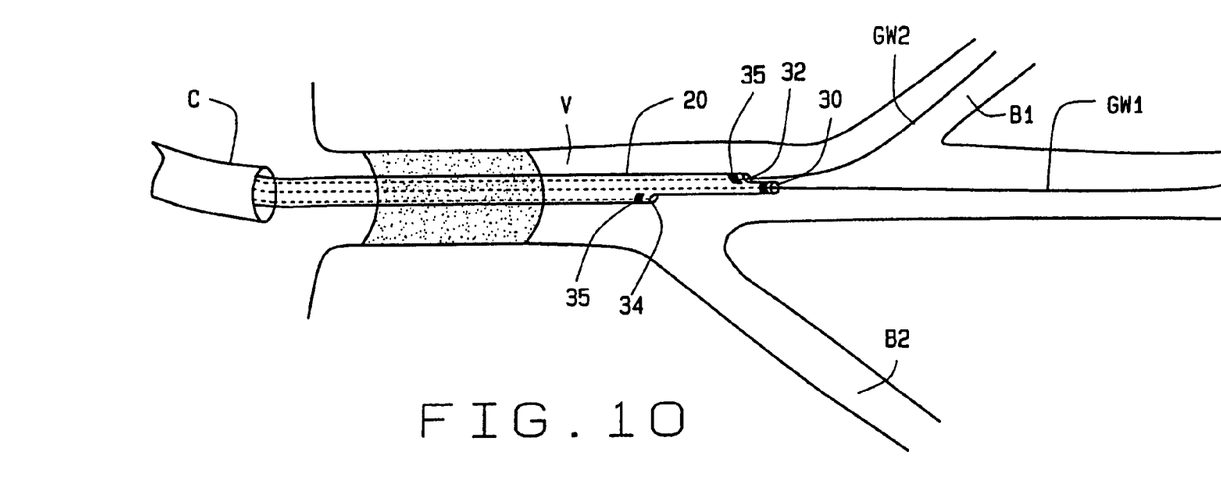
FIG. 10 illustrates the advancement of a second guidewire in a side branch of the artery.
Figure 11:
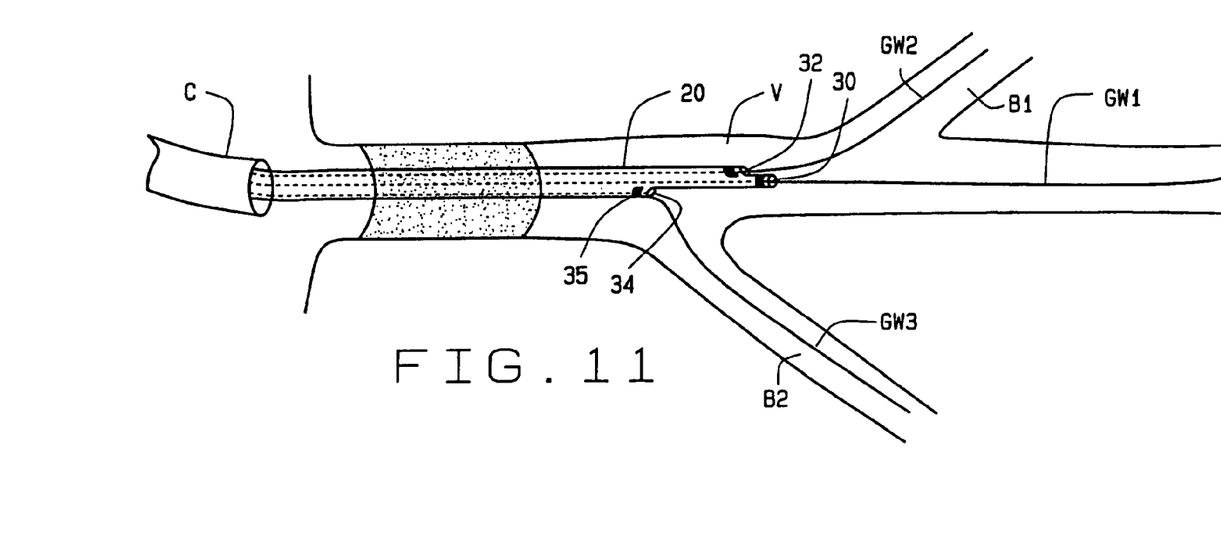
FIG. 11 illustrates the advancement of a second guidewire in a second side branch of the artery.

Referring to FIG. 9, the proximal end of the first guidewire GW1 is introduced into the first lumen through distal opening 30 of a novel catheter 20 (or opening 69 of catheter 60, or opening 86 of catheter 80). Second and third guidewires GW2 and GW3 are positioned within the second and third lumens, for example lumens 26 and 28, from the proximal end of the catheter. Catheter 20 is advanced by riding down the first guidewire GW1. The distal end of catheter 20 is positioned under fluoroscopy with the radio opaque marks 35 visualized to assure proper positioning of the lumen openings 32 and 34. As shown in FIGS. 10 and 11, opening 32 is positioned so that second guidewire GW2 can be advanced into a first side branch B1 of the vessel. Likewise, opening 34 is positioned so that the third guidewire GW3 can be advanced into another side branch B2. It should be noted that with the foregoing procedure, the carrier catheter 20 can function as the guide catheter.

Figure 12:
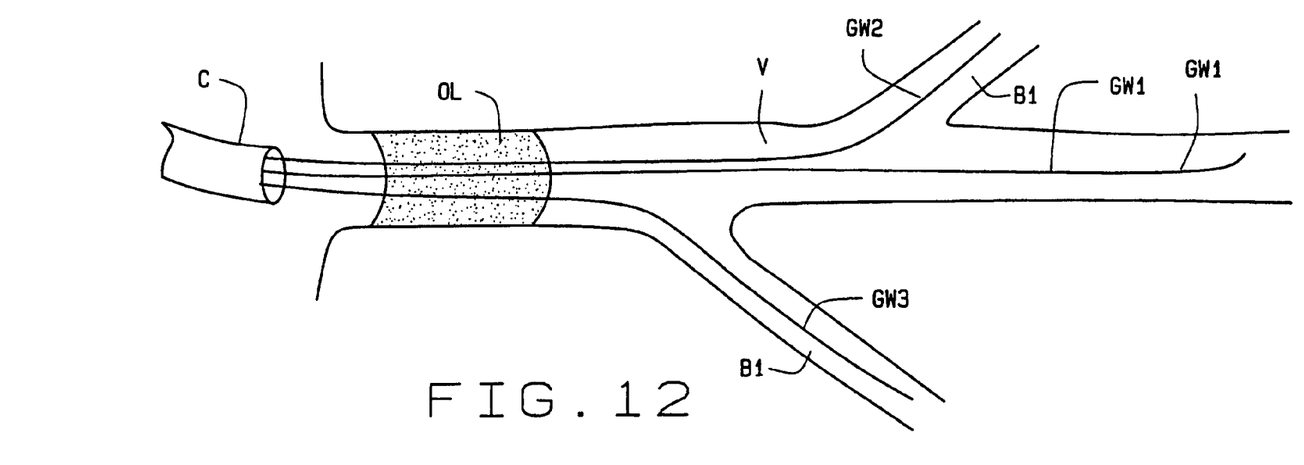
FIG. 12 illustrates the placement of the three guidewires after removal of the catheter of the present invention.
Figure 13:
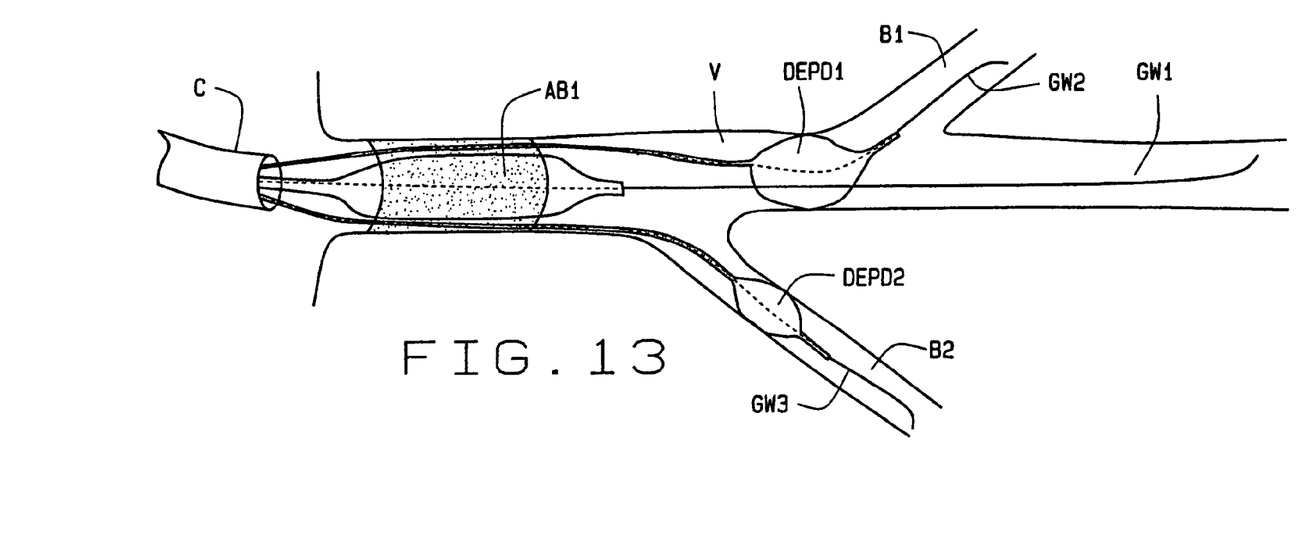
FIG. 13 illustrates the deployment of three separate interventional devices on the guidewires of FIG. 12.
Figure 14:
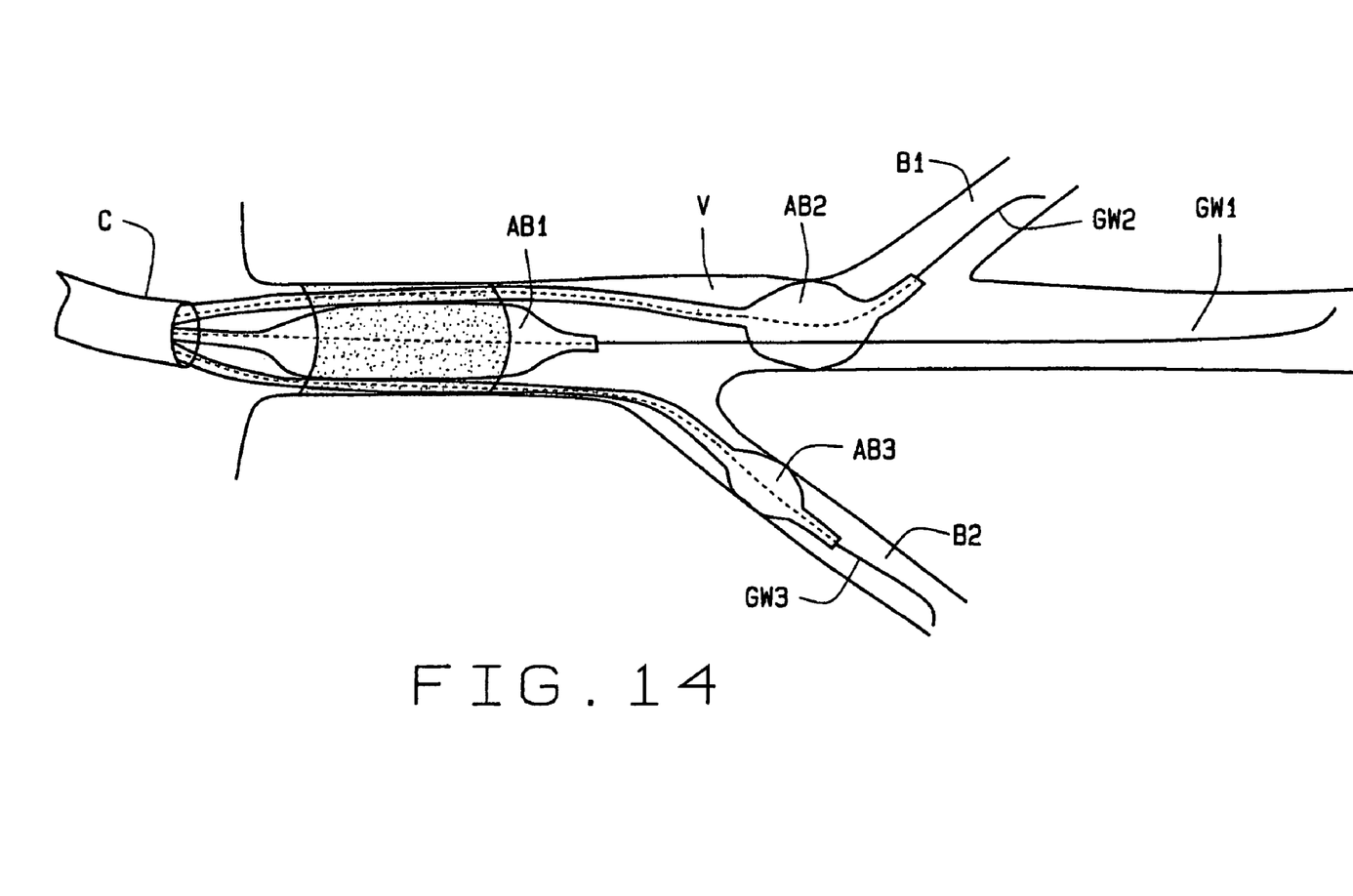
FIG. 14 illustrates the deployment of three separate balloon catheters on the guidewires of FIG. 12.

As seen in FIG. 12, the catheter 20 can be withdrawn and removed, leaving the three guidewires GW1, GW2 and GW3 in position for the introduction of other interventional apparatus as shown in FIG. 13 and FIG. 14.

FIG. 13 illustrates the placement of interventional devices and, in this illustration, the devices are commonly referred to as distal embolization protective devices (DEPDs), shown in the figure as DEPD-1 and DEPD-2. These devices are placed to avoid distal embolization caused by percutanous transluminal coronary angioplasty (PTCA) with a PTCA balloon AB1. Debris is blocked by the inflated DEPD balloon and then aspirated through a catheter. Examples of commercially available exemplary DEPDs include Percusurge® (Purcusurge, Inc., Sunnyvale, Calif., Guardwire Plus™ Temporary Occlusion Catheter (Medtronic, Inc., Minneapolis, Minn.), and FilterWire Ex™ (Boston Scientific EPI, Santa Clara, Calif.). These devices also can function as a common guidewire for the advancement and placement. Each of these representative devices has specific uses and any DEPD disclosed or not disclosed herein is intended for use with the carrier catheter of the present invention.

FIG. 14 represents one exemplary form of interventional apparatus as percutanous transluminal coronary angioplasty (PTCA) balloons AB1, AB2 and AB3, which can be deployed by techniques known to the art over guidewires introduced and positioned using the carrier catheter of the present invention. Any other desired device such as balloons, stents, pressure sensing devices, drug delivery systems or the like may be introduced to the appropriate site by employing one of the three guidewires. As such, the indwelling guidewires GW1, GW2 and GW3 function as dedicated guidewires for future use of catheter borne interventions. The term "dedicated guidewire" is intended to include any guidewire that is placed in a vessel and left for an appreciable amount of time for further use.

The carrier catheter of the present invention can be used to deploy an interventional device that generally is introduced directly into the vasculature or a device that is difficult or impossible to use in the presence of an occlusion Such generally non-catheter borne interventional devices are devoid of a drive or introductory guidewire lumen and, do to their flexibility, cannot be forced across a lesion. Such devices can include a simple fiber optic wire or a pressure or sensing leads such as flow monitoring leads or thermal leads. One example of such a device is the FloWire™ Doppler Guide Wire (EndoSonics Corporation, Rancho Cordova, Calif.).

In any event, in use, the carrier catheter of the present invention positioned with the lead guidewire inside the primary or drive lumen. The lead guidewire can already be dedicated in the vasculature or can be introduced into the primary catheter lumen from the proximal end. The intervention device, for example a pressure flow monitoring lead, is introduced into one of the ancillary lumens, and usually does not extend out of the opening at the distal end. The catheter is advanced down the lead guidewire until the opening of the ancillary lumen is positioned at a predetermined location within the vessel so that the flow monitoring lead is located at the desired location. The carrier catheter can be withdrawn over the guidewire and monitoring lead, leaving the monitoring lead in its predetermined desired location.

As should be appreciated, the fact that the carrier employs the drive guidewire in the primary lumen allows the catheter to pass through any occluded area, carrying the very flexible lead across the lesion inside the ancillary lumen. A second interventional device or an ancillary guidewire can be deployed from a second ancillary lumen, if one is provided on the carrier catheter. In like manner, other interventional devices or combination of guidewires or interventional devices that is desired or useful may be placed with the novel carrier catheter, even in the presence of an occlusion.

As also can be appreciated, with the carrier catheter of the present invention, three guidewires, or combinations of guidewires and interventional devices, can be placed with only one catheter crossing of the lesion OL. This significantly reduces the procedure time and the risk of complications that can occur with multiple crossing of the lesion.

Likewise, each of the exemplary catheters can be used for a rapid exchange of an indwelling catheter into either the primary vessel, the first side branch or second side branch. The indwelling catheter is withdrawn over the appropriate guide wire. The guidewire remains in place and the replacement catheter is advanced along the guidewire. With the catheter of the present invention, one catheter can be used to position three guidewires and those three guidewires can be used to introduce three separate catheters into the vessels, if desired. Further, with the primary guidewire GW1 is left in place a novel catheter of the present invention can have non-catheter borne devices or devices that heretofore unsuited for crossing an occlusive lesion loaded in the ancillary lumens. The catheter is deployed by riding down the primary guidewire so that the user can deploy these type devices in a desired location.

The catheter of the present invention can be used for rapid exchange of a dedicated guidewire. If the physician desires to exchange dedicated guidewire GW1, for example, he can place lumen 24 of a catheter 20 over guidewire GW1 and can introduce a replacement guidewire into adjacent lumen 26. He can advance the catheter along GW1 until opening 32 of lumen 26 is distal to or beyond the branches B1 and B2, if that is the structure of the vessel. In any event, he advances the catheter 20 until opening 32 of lumen 26 is adjacent the distal end of GW1 so that the distal end of the replacement guidewire is positioned approximately where the distal end of GW1 is positioned. He then can withdraw old guidewire GW1 through the proximal end of lumen 24. Subsequently, he can withdraw the catheter over the replacement guidewire leaving the replacement guidewire in the parent vessel in the approximate location of the removed guidewire.

By using any one of the exemplary embodiments of the carrier catheter of the present invention, the practitioner can replace a dedicated guidewire with only one maneuver, avoiding the risks associated with multiple crossings of a lesion with guidewires. It will be appreciated that either catheter 20, 60 or 80 can be used in the above procedures. It will be noted that catheter 60, FIGS. 3-5, is particularly well adapted to the rapid changing of dedicated or indwelling guidewires and catheters.

From the foregoing it can be appreciated that the novel carrier catheter of the present invention exhibits exceptional versatility, safety and ease of use. The device can be employed to deploy the devices previously described and the guidewires can be employed for the deployment of other, non-catheter borne devices such as fiber optic wires, pressure or flow measurement leads or the like, particularly to a site beyond an occlusion. Although the catheter of the present invention is illustrated having three (3) lumens to accommodate three (3) guidewires, the catheter of the present invention can be constructed to have two lumens or more than three lumens. A catheter with any number of lumens is intended by encompassed by the claims to the instant invention.

The foregoing description of the exemplary embodiments and accompanying drawings are intended to be illustrative only, with various changes and modifications encompassed by the appended claims and, therefore, should not be construed in a limiting sense.

The invention claimed is:

1. A carrier catheter for use in a biological conduit within the body of a subject, comprising: a flexible body including a first lumen formed longitudinally therein, said first lumen having an opening therein at a proximal end and an opening therein at a distal end, said body having at least a second lumen formed longitudinally therein, said second lumen having an opening therein at a proximal end and an opening therein at a distal end, each of said recited openings in the distal ends of said lumens facing the longitudinal direction of the catheter and being positioned so that a guidewire advanced through any one of said recited lumens is positioned a predetermined location within the vessel; and an elongated introductory apparatus at a proximal end of the flexible body having a cross section substantially less in width than a cross sectional width of the flexible body, the introductory apparatus being sufficiently rigid to allow introduction of the flexible body into the biological conduit.

2. The carrier catheter of claim 1, wherein said body further includes a third lumen formed longitudinally therein, said third lumen having an opening therein at a proximal end and an opening therein at a distal end.

3. The carrier catheter of claim 2, wherein said openings in said proximal ends of said first, second and third lumens are aligned in a same plane.

4. The carrier catheter of claim 2, wherein said openings in the distal ends of said second and third lumens are proximal to the opening in the distal end of the second lumen.

5. The carrier catheter of claim 4, wherein said opening in the distal end of said third lumen is proximal to the opening in the distal end of the second lumen.

6. The carrier catheter of claim 1, wherein said introductory apparatus is a push-wire.

7. The carrier catheter of claim 1, wherein said introductory apparatus further comprises a filling on a proximal end.

8. The carrier catheter of claim 1, further comprising radio-opaque markers along the length of the body to facilitate placement of the catheter.

9. A carrier catheter for use in placement of guidewires or interventional devices at a predetermined position within a vessel in the body of a subject, comprising: a body and a concentric, elongated, substantially rigid introductory apparatus at a proximal end of the body, said body further including a first lumen structure, said first lumen structure having an opening therein at a proximal end and an opening therein at a distal end, said body having at least a second lumen, said at least second lumen structure having an opening therein at a proximal end and an opening therein at a distal end proximal to said opening in said distal end of said first lumen, said recited openings in the distal ends of said lumens being positioned so that a guidewire or interventional device advanced through any one of said recited lumen structured is positioned at the predetermined location within the vessel.

10. The carrier catheter of claim 9, wherein said body includes a third lumen structure, said third lumen structure having an opening therein at a proximal end and an opening therein at a distal end proximal to said opening in said distal end of said first lumen structure.

11. The carrier catheter of claim 10, wherein said at least second lumen and said third lumen are expandable.

12. The carrier catheter of claim 9, wherein said first and said at least second lumens are tapered.

13. The carrier catheter of claim 9, wherein a proximal end of said substantially rigid introductory apparatus further comprises a fitting.

14. The carrier catheter of claim 9, further comprising a plurality of markers to facilitate positioning of said recited openings in the distal ends of the recited lumens at the predetermined location within the vessel.

15. The carrier catheter of claim 9 wherein said substantially rigid introductory apparatus is a push-wire sufficiently rigid to allow introduction of the catheter body into a vessel or artery but not so inflexible as to cause an undue risk of dissection of the vessel or artery during use.

16. A carrier catheter for use in placement of guidewires or interventional devices at a predetermined position within a vessel in the body of a subject, comprising:
a flexible body with an integral push-wire at a proximal end thereof for introducing the flexible body into a vessel, said body further comprising a main lumen structure, said main lumen having an opening therein at a proximal end and an opening therein at a distal end, at least a second lumen, said at least second lumen having an opening therein at a proximal end and an opening therein at a distal end, at least a third lumen, said at least third lumen having an opening therein at a proximal end and an opening at a distal end, said recited openings in the distal ends of said recited lumens being positioned so that a guidewire or interventional device advanced through any one of said recited lumen structured is positioned at the predetermined location within the vessel, said body further comprising a plurality of markers to facilitate positioning of said recited openings in the distal ends of the recited lumens at the predetermined location within the vessel or artery.

17. The carrier catheter of claim 16 wherein said integral push-wire is formed from steel.

18. The carrier catheter of claim 16 wherein said integral push-wire includes a connector at its proximal end.

19. A carrier catheter for use in introduction or quick exchange of guidewires or interventional devices within a vessel in the body of a subject, comprising:
a proximal section and a distal body section;
wherein said proximal section comprises an elongated push-wire for introducing the distal body section into a vessel; and
wherein said distal body section comprises a main lumen with an opening at a proximal end and an opening at a distal end, at least a second lumen with an opening at a proximal end and an opening at a distal end, said recited openings in the distal ends of said lumens facing the longitudinal direction of the catheter and being positioned on the catheter so that a guidewire or interventional device advanced through any one of said recited lumens is positioned at a predetermined location within the vessel, and a plurality of markers to facilitate positioning of said recited openings in the distal ends of the recited lumens at the predetermined location within the vessel or artery.

20. The carrier catheter of claim 19 wherein said distal body section comprises at least a third lumen with an opening at a proximal end and an opening at a distal end.

* * * * *

UNITED STATES PATENT AND TRADEMARK OFFICE
CERTIFICATE OF CORRECTION

PATENT NO. : 7,645,273 B2 Page 1 of 1
APPLICATION NO. : 10/469673
DATED : January 12, 2010
INVENTOR(S) : Alessandro Lualdi It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1615 days.

Signed and Sealed this

Twenty-first Day of December, 2010

David J. Kappos
*Director of the United States Patent and Trademark Office*